United States Patent

Toda et al.

[11] Patent Number: 5,043,495
[45] Date of Patent: Aug. 27, 1991

[54] PROCESS OF SEPARATION AND PURIFICATION OF A PROPARGYL ALCOHOLS

[75] Inventors: Fumio Toda, Ehime; Koichi Tanaka, Matsuyama; Kikuo Ataka, Ube, all of Japan

[73] Assignee: Ube Industries, Ltd., Ube, Japan

[21] Appl. No.: 475,892

[22] Filed: Jan. 30, 1990

Related U.S. Application Data

[62] Division of Ser. No. 79,821, Jul. 30, 1987, Pat. No. 4,918,190.

[30] Foreign Application Priority Data

Aug. 6, 1986 [JP] Japan .................... 61-183347

[51] Int. Cl.⁵ .................... C07B 63/02; C07C 33/28; C07C 33/30; C07C 33/042
[52] U.S. Cl. .................... 568/809; 568/807; 568/810; 568/816; 568/828; 568/838; 568/873
[58] Field of Search ........... 568/809, 810, 807, 816, 568/828, 838, 873

[56] References Cited

U.S. PATENT DOCUMENTS 4,467,102 8/1984 Toda et al. .................... 547/78

OTHER PUBLICATIONS

Toda et al., Tet. Letters 22, 4669 (1981).
Toda, JCS Chem Comm 743 (1983).
Yabuki, Chem. Letters 1988, 749.
Ube Industries, Ltd., Chem. Abs. 101, 130376 (1984).
Toda et al II, Chemistry Letters 1905, 1986.
Toda et al. III, Chem Abs 100, 5961g (1983).
Hart et al., Nippon Kagaku Kaishi, 2, 239–42 (1983).
Toda IV, Isr. J Chem vol. 25, pp.338–345 (1985).

*Primary Examiner*—Mark L. Berch

[57] ABSTRACT

A process of separation and purification of a propargyl alcohol which comprises treating a propargyl alcohol represented by Formula (I):

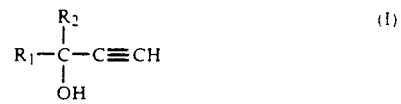

wherein each of $R_1$ and $R_2$ represents a substituent which is different from each other, and is selected from the group consisting of a $C_1$–$C_8$ alkyl group, a phenyl group; a halophenyl group, a phenyl group having at least one methyl substituent, an aralkyl group and a cycloalkyl group, which is chemically or optically impure, with a tertiary diamine represented by Formula (II):

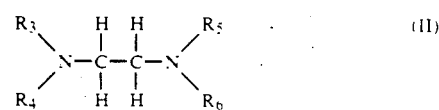

wherein each of $R_3$, $R_4$, $R_5$ and $R_6$ may be the same or different and represents an aralkyl group or an alkyl group having 1 to 6 carbon atoms; and $R_3$, $R_4$, $R_5$ and $R_6$ may be bonded to each other, to form a crystalline complex compound of the propargyl alcohol represented by Formula (I) and the tertiary diamine represented by Formula (II), separating and purifying the resulting compound, and treating the resultant compound with an acid to isolate the propargyl alcohol represented by Formula (I).

13 Claims, No Drawings

PROCESS OF SEPARATION AND PURIFICATION OF A PROPARGYL ALCOHOLS

This is a division of application Ser. No. 07/079,821, filed July 30, 1987, now U.S. Pat. No. 4,918,190, issued Apr. 17, 1990.

BACKGROUND OF THE INVENTION

This invention relates to a crystalline complex compound of a propargyl alcohol and a tertiary diamine and a process for separating and purifying the propargyl alcohol into a chemically or optically pure form by use of the complex compound.

A propargyl alcohol represented by the Formula (I):

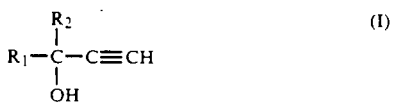

wherein each of $R_1$ and $R_2$ represents a substituent which is different from each other is an important compound as a starting material of an optically active hexa-2,4-diyne-1,6-diol. The optically active hexa-2,4-diyne-1,6-diol is an optical resoluting agent for a wide variety of compounds utilizing a specific inclusion (clathrate) phenomenon. Particularly, its utilization is expected for an optical resolution of raw materials of medicines and agricultural drugs (J. Amer. Chem. Soc., 105, P.5151, 1983; Tetrahedron Letters, 22, P.4669, 1981; Chemistry Letters, P.885, 1985; and Japanese Unexamined Patent Publication No. 169434/1985).

As those which form a crystalline complex compound with the above-mentioned propargyl alcohol, there have conventionally been known brucine and sparteine which are natural substances. By use of a crystalline complex compound of said propargyl alcohol and these natural substances, an optical resolution of the optically active propargyl alcohol has been carried out (see U.S. Pat. No. 4,467,102/1984; Japanese Unexamined Patent Publication No. 55840/1984; Toda, Topics in Current Chemistry, vol.140, p44, 1987).

However, in view of the economical point, it is impossible to use such an expensive natural substance as brucine and sparteine to carry out, in an industrial scale, the chemical purification of the compound represented by Formula (I). Accordingly, a purification process which may be readily conducted at lower cost and in an industrial scale is required.

The optical resolution of the compound represented by Formula (I) has been carried out using the natural substances as mentioned above. However, according to such a method, even if any one of the above natural substances is used, it is only one of enantiomers that can be obtained in a high purity, and a complex compound using another enantiomer and a natural substance is obtained in an optical purity of as low as 60 to 80 %, since it is poor in crystallizability and is difficult to be purified. Using a compound represented by Formula (I) which is of low optical purity, a hexa-2,4-diyne-1,6-diol is produced to give an optically inactive meso-type substance in addition to the desired optically active hexa-2,4-diyne-1,6-diol According to the conventional methods, it is not easy to remove this meso substance and thus recrystallization process is required for several times. Therefore, it has been substantially extremely difficult to produce enantiomers of hexa-2,4-diyne-1,6-diols, both of which are of high purity.

Further, the propargyl alcohol represented by Formula (I) is a compound which is usually in a liquid form around room temperature or has its melting point close to room temperature. Therefore, purification by crystallization is not practical due to large loss of the compound Purification by distillation cannot be adopted since said propargyl alcohols are not thermostable. For these reasons, as a chemical purification method for said compound, a laboratorial method such as column chromatography etc. is usually adopted.

THE SUMMARY OF THE INVENTION

An object of this invention is to provide a process for purifying a propargyl alcohol into a chemically and optically pure form, which is possibly carried out at a low cost, with readiness and in an industrial scale, by forming a crystalline complex compound of a propargyl alcohol which is chemically and optically impure, with a tertiary diamine.

The separation and purification process of this invention is characterized in that a propargyl alcohol represented by Formula (I):

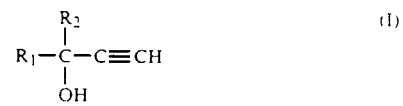

wherein each of $R_1$ and $R_2$ represents a substituent which is different from each other
which is chemically or optically impure, is treated with a tertiary diamine represented by Formula (II):

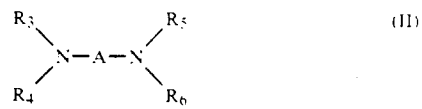

wherein A represents a group having two carbon atoms as a chain member which may be branched; each of $R_3$, $R_4$, $R_5$ and $R_6$ may be the same or different and represents an aralkyl group or an alkyl group having 1 to 6 carbon atoms; and A, $R_3$, $R_4$, $R_5$ and $R_6$ may be bonded to each other,
to form a crystalline complex compound of the propargyl alcohol represented by Formula (I) and the tertiary diamine represented by Formula (II), and after separation and purification of the resulting compound, the compound is treated with an acid to isolate the propargyl alcohol represented by Formula (I).

DESCRIPTION OF PREFERRED EMBODIMENT OF THE INVENTION

In Formula (I), $R_1$ and $R_2$ represent a substituent which is from different each other. Such substituent may be any one so long as it is stable under acidic conditions (a diluted acid is usually used) where said compound (I) is isolated from the crystalline complex compound formed, and may include, for example, an alkyl group having 1 to 8 carbon atoms such as methyl, ethyl, t-butyl, octyl, etc.; an aryl group such as phenyl, 2-chlorophenyl, 2-bromophenyl, 2-fluorophenyl, 3-chlorophenyl, 3-bromophenyl, 3-fluorophenyl, 4-chlorophenyl, 4-bromophenyl, 4-fluorophenyl, 2-methylphenyl, 3-methylphenyl, 4-methylphenyl, 2,3- dimethylphenyl, 2,4-dimethylphenyl, 2,5-dimethylphenyl, 2,6-dimethylphenyl, 3,4-dimethylphenyl, 3,5-dimethylphenyl, etc.; an aralkyl group such as benzyl etc.; and a cycloalkyl group such as cyclopentyl, cyclohexyl, etc.

The tertiary diamine represented by the above Formula (II) may include, for example, 1,4-diazabicyclo[2.2.2]octane (triethylenediamine), 2-methyl-1,4-diazabicyclo[2.2.2]octane, 2,3-dimethyl-1,4-diazabicyclo[2.2.2]octane, 2,6-dimethyl-1,4-diazabicyclo[2.2.2]octane, 2-phenyl-1,4-diazabicyclo[2.2.2]octane, N,N'-dimethylpiperazine, N,N'-diethylpiperazine, N,N'-diisopropylpiperazine, 2-methyl-N,N'-dimethylpiperazine, N,N,N',N'-tetramethylethylenediamine, N,N,N',N'-tetraethylethylenediamine, N,N,N',N'-tetramethyl-1,2-propanediamine, N,N,N',N'-tetraethyl-1,2-propanediamine, N,N,N',N'-tetramethyl-1,2-butanediamine, octahydrodipyrrolo[1,2a;1',2'-d]pyrazine, N-(N'-methyl-2-pyrrolidinyl)methylpiperidine and the like.

In cases where the compound of Formula (I) and the compound of Formula (II) are reacted, the proportion of the compound (I) to the compound (II) is preferably in the range of 1 : 1.5 to 1 : 0.4 in terms of molar ratio. Reaction is usually carried out in a solvent such as an alcohol series solvent, e.g. methanol, ethanol, propanol, isopropanol, butanol, isobutanol, etc.; an ether series solvent, e.g. ethyl ether, dioxane, tetrahydrofuran, etc.; a hydrocarbon series solvent, e.g. cyclohexane, benzene, toluene, etc.; clorine series solvent, e.g. dichloromethane, chloroform, etc.

Since the reaction proceeds rapidly at room temperature, neither heating nor cooling is particularly required. There is no specific limitation of concentration of the reaction mixture, but a solvent is preferably used in an amount equal to the sum of the weight of the compound of Formula (I) and the compound of the Formula (II) to 10-fold thereof. After completion of the reaction, the mixture is allowed to stand at room temperature, or preferably by cooling it to around 0° C., a crystal may be allowed to be precipitated. In order to carry out an optical purification of the compound of Formula (I), it is necessary to limit an amount of the crystal pricipitated in accordance with the optical purity of the starting material used.

The thus obtained crystal can be isolated by a method such as filtration etc. In cases where the compound of Formula (II) used is not voluminous, a complex compound obtained has usually a composition ratio of 1 molecule of the compound of Formula (II) relative to 2 molecules of the compound of Formula (I).

Liberation of the compound of Formula (I) from the resulting complex compound may be carried out by dissolving or suspending the complex compound in an appropriate non-water-soluble organic solvent, followed by addition of a diluted acid thereto. Consequently, the compound of Formula (I) is extracted in the organic solvent as a purified form. The non-water-soluble organic solvent to be used may include benzene, toluene, ethyl ether, dichloromethane, chloroform, cyclohexane, etc. The diluted acid may include diluted hydrochloric acid, diluted sulfuric acid, diluted phosphoric acid, etc. The acid may preferably be used in an amount of 1-fold equivalent to 10-fold equivalent to an amount of a diamine contained in the complex compound. The reaction proceeds rapidly at room temperature and heating is not necessary. The reaction usually completes within 30 minutes. The concentration of the reaction mixture is not particularly limitative.

The organic solvent is removed from the thus obtained organic solvent containing the compound of Formula (I) to isolate the compound of Formula (I) in a purified form. By this procedure only, it is possible to obtain a compound which is of a sufficiently high purity and therefore other purification procedure is not required at all. The same will be applied in cases where an optical purification is carried out.

EXAMPLES

In the following, this invention will be described in more detail by referring to Examples, but the scope of this invention is not limited thereto.

EXAMPLE 1

In 7 ml of isopropanol, 7.5 g of ($\pm$) 1-(2-chlorophenyl)-1-phenylpropargyl alcohol (hereinafter referred to "Compound (A)") and 3.5 g of 1,4-diazabicyclo[2.2.2]-octane were stirred at room temperature to precipitate immediately a colorless solid. This solid was filtered off and washed with a small amount of isopropanol, followed by drying. Yield: 8.0 g. From the result of measurement by proton NMR, this compound was found to be a complex compound of Compound (A) and 1,4-diazabicyclo[2.2.2]octane having a composition ratio of 2 : 1. m.p: 126 to 129° C.

NMR (CDCl$_3$, $\delta$ ppm) 8.05 (d; 1H), 7.5 (m; 2H), 7.3(m; 6H) (the above-mentioned are aromatic ring proton), 5.75(br; 1H, —OH), 2.82(s; 1H, C≡CH), 2.60 (s; 6H, —CH$_2$—).

Elemental analysis C: 71.97%, H: 5.71%, N: 4.71%.
Calculated value C: 72.35%, H: 5.73%, N: 4.72%.

EXAMPLE 2

To 15 ml of isopropanol, were added 8.0 g of ($\pm$)-Compound (A) (containing 15% of 1,4-bis(2-chlorophenyl)-1,4-diphenyl-but-2-yne-1,4-diol as an impurity) which is 80 % in chemical purity and 3.7 g of 1,4-diazabicyclo[2.2.2]octane, followed by heating of the mixture to 65° C. Impurities were removed by filtration during heating and the filtrate was allowed to stand at room temperature to precipitate a crystal. Yield: 6.0 g. The crystal was identical to that obtained in Example 1.

In 15 ml of dichloromethane, 3.5 g of the crystal thus obtained was suspended and to the suspension was added 5 ml of 4N-sulfuric acid, followed by stirring of the mixture for 30 minutes. After the organic layer was separated and dried, dichloromethane was removed under reduced pressure to give 2.8 g of colorless oil. According to NMR and IR spectrals and gas chromatography, this oil was found to be ($\pm$)-Compound (A) which was almost pure (99% or higher). The oil was allowed to stand at room temperature for several days to be solidified. m.p.: 42 to 43° C.

EXAMPLE 3

To 7 ml of methanol, 7.5 g of Compound (A) in which (+) type substance is contained in an excessive amount (80% ee) and 3.5 g of 1,4-diazabicyclo[2.2.2]octane were added, followed by stirring of the mixture at room temperature to precipitate a colorless crystal. The crystal was filtered off and crystallized again from 5 ml of methanol. Then 2.5 g of colorless crystal was obtained. As a result of NMR spectrum, the crystal was identical to the compound obtained in Example 1. m.p.: 138 to 141° C.

$[\alpha]_D^{20} = 110°$ (c=1, MeOH).

To a mixture of 2.5 g of the thus obtained compound and 10 ml of ethyl ether was added 4 ml of 4N-sulfuric acid, followed by stirring of the resulting mixture for 30 minutes. After the organic layer was separated and dried, ethyl ether was removed under reduced pressure to give 2.0 g of a colorless oil. According to the same procedure as in Example 2, the oil was confirmed to be Compound (A). The Compound (A) indicated $[\alpha]_D^{20} = +138°$ (c=1, MeOH) and its optical purity was 100%.

EXAMPLE 4

The same procedure was repeated as in Example 1 except that 7.5 g of ($\pm$) Compound (A) (optical purity: 100%) and 3.5 g of N,N,N'N'-tetramethylethylenediamine as a diamine were used.

There was obtained 7.8 g of ($\pm$) Compound (A) ½ N,N,-N'N'-tetramethylethylenediamine complex. m.p.: 112 to 114° C.

NMR 8.0 (d; 1H), 7.52 (m; 2H), 7.30(m; 6H) (the above-mentioned are aromatic ring proton), 4.25(br; 1H, —OH), 2.86(s; 1H, C≡CH), 2.35 (s; 2H, CH$_2$), 2.18 (s; 6H, CH$_3$).

EXAMPLE 5

The same procedure was repeated as in Example 4 except that 3.5 g of N,N'-dimethylpiperazine as a diamine was used. There was obtained 8.1 g of ($\pm$) Compound (A) ½ N,N'-dimethylpiperazine complex. m.p.: 124 to 125° C.

EXAMPLE 6

To 5 ml of isopropanol was added 0.485 g of ($\pm$)-Compound (A) and 0.332 g of octahydrodipyrrolo[1,2-a;1',2'-d]pyrazine and the resulting mixture was heated to 60° C. to be dissolved. The resulting solution was allowed to stand at room temperature for cooling to give 0.53 g of a pale yellow crystal. m.p.: 114 to 117° C.

Elemental analysis C: 73.63%, H: 6.31%, N:4.36%.

Calculated value as Compound (A).½ octahydrodipyrrolo[1,2-a;1',2'-d]pyrazine C: 73.72%, H: 6.19%, N:4.30%.

EXAMPLE 7

The same procedure was repeated as in Example 1 except that 8.9 g of ($\pm$) 1-(4-bromophenyl)-1-phenylpropargyl alcohol was used to obtain 8.2 g of 1-(4-bromophenyl)-1-alcohol. ½ triethylenediamine complex. The melting point of the substance which was recrystallized from methanol was 74 to 75° C.

EXAMPLE 8

The same procedure was repeated as in Example 3 except that 9.0 g of 78.4 %ee (+) 1-(2-bromophenyl)-1-phenylpropargyl alcohol was used to obtain 4.0 g of 1-(2-bromophenyl)-1-phenylpropargyl alcohol. ½ triethylenediamine complex. m.p.: 133 to 136° C. Liberation of the alcohol was carried out by the same procedure as in Example 3 to give 3.3 g of 100 %ee (+) 1-(2-bromophenyl)-1-phenylpropargyl alcohol.

$[\alpha]_D^{20} = +139°$ C. (c=1, MeOH).

EXAMPLE 9

The same procedure was repeated as in Example 5 except that 6.9 g of 51.8 %ee (+) 1-(2-fluorophenyl)-1-phenylpropargyl alcohol was used to obtain 4.4 g of 1-(2-fluorophenyl)-1-phenylpropargyl alcohol. ½ N,N'-dimethylpiperazine complex. m.p.: 107 to 112° C. From the filtrate, 3.3 g of 99.4 %ee (+) 1-(2-fluorophenyl)-1-phenylpropargyl alcohol was obtained.

EXAMPLE 10

The same procedure was repeated as in Example 3 except that 7.0 g of 43.8 %ee (+) 1-(2,4-dimethylphenyl)-1-phenylpropargyl alcohol was used to obtain 4.0 g of 1-(2,4-dimethylphenyl)-1-phenylpropargyl alcohol. ½ triethylenediamine complex. m.p.: 60 to 62° C. Liberation of the alcohol was carried out by the same procedure as in Example 3 to give 3.1 g of racemic 1-(2,4-dimethylphenyl)-1-phenylpropargyl alcohol. From the filtrate, 3.0 g of 60.2 %ee (+) 1-(2,4-dimethylphenyl)-1-phenylpropargyl alcohol was obtained.

EXAMPLE 11

To 5 ml of methanol, 0.86 g of N,N'-diisopropylpiperazine and 0.89 g of 32.3 %ee (+) 1-t-butyl-1-phenylpropargyl alcohol were added, following by stirring of the mixture at room temperature for 12 hours to precipitate 0.55 g of 1-t-butyl-1-phenylpropargyl alcohol. ½ N,N'-diisopropylipierazine complex as colorless crystals. m.p.: 78 to 80° C. The alcohol liberated from the complex was found to b racemic, but 0.48 g of 46.3 %ee (+) 1-t-butyl-1-phenylpropargyl alcohol was obtained from the filtrate.

We claim:

1. A process of separation and purification of a propargyl alcohol which comprises treating a propargyl alcohol represented by formula (I):

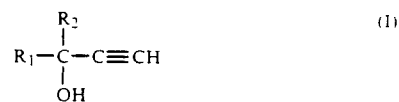

wherein each of $R_1$ and $R_2$ represents a substituent which is different from each other, and is selected from the group consisting of a $C_1$-$C_8$ alkyl group, a phenyl group substituted one or two times by Cl, Br, F or 2,4-dimethyl, a benzyl group and a $C_3$-$C_6$ cycloalkyl group, which is chemically or optically impure, with a tertiary diamine selected from the group consisting of 1,4-diazabicyclo(2.2.2) octane, 2-methyl-1,4-diazabicyclo(2.2.2) octane, 2,3-dimethyl-1,4-diazabicyclo-(2.2.2)octane, 2,6-dimethyl-1,4-diazabicyclo(2.2.-2)octane, 2-phenyl-1,4-diazabicyclo(2.2.2)octane, N,N'-dimethylpiperazine, N,N'-diethylpiperazine, N,N'-diisopropylpiperazine, 2-methyl-N,N'-dimethylpiperazine, N,N,N',N'-tetramethylethylenediamine, N,N,N',N'-tetraethylethylenediamine, N,N,N',N'-tetramethyl-1,2-propanediamine, N,N,N',N'-tetraethyl-1,2-propanediamine and N,N,N',N'-tetramethyl-1,2-butanediamine, to form a crystalline complex compound of the propargyl alcohol represented by formula (I) and the tertiary diamine, separating and purifying the resulting compound, and treating said resulting compound with an acid to isolate the propargyl alcohol represented by formula (I).

2. The process according to claim 1, wherein said propargyl alcohol compounds is 1-(2-chlorophenyl)-1-phenylpropargyl alcohol; 1-(4-bromophenyl)-1-phenylpropargyl alcohol; 1-(2-bromophenyl)-1-phenylpropargyl alcohol; 1-(2-fluorophenyl)-1-phenylpropargyl alcohol; 1-(2,4-dimethylphenyl)-1-phenylpropargyl alcohol; or 1-t-butyl-1-phenylpropargyl alcohol.

3. The process according to claim 1, wherein the complex is 2:1 ratio complex of 1-(2-chlorophenyl)-1-phenylpropargyl alcohol and 1,4-diazabicyclo-octane; 1-(4-bromophenyl)-1-phenylpropargyl alcohol and triethylenediamine; 1-(2-fluorophenyl)-1-phenylpropargyl alcohol and N,N'-dimethylpiperazine; 1-(2-bromophenyl)-1-phenylpropargyl alcohol and triethylenediamine complex; 1-(2,4-dimethylphenyl)-1-phenylpropargyl alcohol and triethylenediamine complex; or 1-t-butyl-1-phenylpropargyl alcohol and N,N'-diisopropylpiperazine.

4. The process according to claim 1, wherein the crystalline complex comprises two molecules of the propargyl alcohol and one molecule of the tertiary diamine.

5. The process according to claim 1, wherein said acid used for isolation of the propargyl alcohol from the complex compound is selected from the group consisting of hydrochloric acid, sulfuric acid and phosphoric acid.

6. The process according to claim 1 wherein said acid is used in an amount of 1-fold equivalent to 10-fold equivalent to an amount of the diamine contained in the complex compound.

7. The process according to claim 1, wherein said $R_1$ or $R_2$ in formula (I) is selected from the group consisting of methyl, ethyl, t-butyl, octyl, 2-chlorophenyl, 2-bromophenyl, 2-fluorophenyl, 3-chlorophenyl, 3-bromophenyl, 3-fluorophenyl, 4-chlorophenyl, 4-bromophenyl, 4-fluorophenyl, 2,4-dimethylphenyl, benzyl, cyclopentyl and cyclohexyl.

8. The process according to claim 7, wherein said $R_1$ or $R_2$ in formula (I) is 2-chlorophenyl.

9. The process according to claim 1, wherein said crystalline complex compound formed is extracted, for its liberation, with a non-water-soluble organic solvent selected from the group consisting of benzene, toluene, ethyl ether, dichloromethane, chloroform and cyclohexane.

10. The process according to claim 1, wherein said tertiary diamine is selected from the group consisting of 1,4-diazabicyclo-octane, N,N'-dimethylpiperazine and N,N,N',N'-tetramethylethylenediamine.

11. The process according to claim 1, wherein the proportion of said propargyl alcohol represented by formula (I) to said tertiary diamine is in the range of 1 : 1.5 to 1 : 0.4 in terms of molar ratio.

12. The process according to claim 1, wherein said process is carried out in a solvent selected from the group consisting of methanol, ethanol, propanol, isopropanol, butanol, isobutanol, ethyl ether, dioxane, tetrahydrofuran, cyclohexane, benzene, toluene, dichloromethane and chloroform.

13. The process according to claim 12, wherein said solvent is used in an amount of 1-fold equivalent to 10-fold equivalent to the sum of the weight of the propargyl alcohol represented by Formula (I) and the tertiary diamine represented by Formula (II).

* * * * *